United States Patent [19]

Crump et al.

[11] Patent Number: 4,518,777
[45] Date of Patent: May 21, 1985

[54] METHYLENE PHOSPHONIC ACID SCALE INHIBITOR COMPOSITIONS DERIVED FROM AMINOHYDROCARCARBYLPIPERAZINE UREA ADDUCTS

[75] Inventors: Druce K. Crump, Lake Jackson; David A. Wilson, Richwood, both of Tex.

[73] Assignee: The Dow Chemical Company, Midland, Mich.

[21] Appl. No.: 528,835

[22] Filed: Sep. 2, 1983

[51] Int. Cl.³ .................. C07D 241/04; C07D 403/12; C02F 5/14
[52] U.S. Cl. .................................. 544/337; 210/700; 252/82; 252/180
[58] Field of Search .......................................... 544/337

[56] References Cited

U.S. PATENT DOCUMENTS

| | | | |
|---|---|---|---|
| 2,599,807 | 6/1952 | Bersworth | 260/502.5 R |
| 2,609,390 | 9/1952 | Bersworth | 260/502.5 R |
| 3,288,846 | 11/1966 | Irani et al. | 260/502.5 R |
| 3,331,773 | 7/1967 | Gunderson et al. | 210/698 |
| 3,336,221 | 8/1967 | Ralston | 210/700 |
| 3,434,969 | 3/1969 | Ralston | 210/700 |
| 3,674,804 | 7/1972 | Redmore | 544/337 |
| 3,720,498 | 3/1973 | Redmore | 252/389 A |
| 3,743,603 | 7/1973 | Redmore | 252/180 |
| 3,859,211 | 1/1975 | Redmore | 210/729 |
| 3,954,761 | 5/1976 | Redmore | 544/337 |
| 4,051,110 | 9/1977 | Quinlan | 252/389 A |
| 4,055,591 | 10/1977 | Scharf | 260/465 A |

OTHER PUBLICATIONS

"Toward a Better Understanding of Commercial Organophosphonates", Roderick A. Campbell, Proced. Int. Water Conf., Eng. Soc. West PA, 41, pp. 167–174, (1980).
"Scale and Deposit Control in Cooling Water Systems", Jeffrey R. Townsend, Karl W. Heiman, Proced. Int. Water Conf., Eng. Soc. West PA, 39, pp. 89–99, (1978).

Primary Examiner—Donald G. Daus
Assistant Examiner—William A. Teoli, Jr.
Attorney, Agent, or Firm—A. C. Ancona

[57] ABSTRACT

Certain methylene phosphonic acid derivatives of aminohydrocarbyl piperazine-urea adducts are good threshold agents to prevent metal ion precipitation in aqueous solutions. These derivatives have the formula

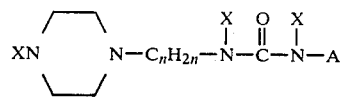

wherein A is

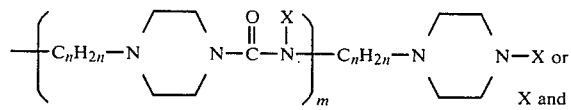

wherein X is

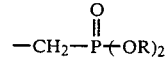

or H and wherein R is H, ammonium, an alkali or alkaline earth metal, m is 0-2, n is 2 or 3 and wherein at least one X is

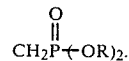

19 Claims, No Drawings

METHYLENE PHOSPHONIC ACID SCALE INHIBITOR COMPOSITIONS DERIVED FROM AMINOHYDROCARCARBYLPIPERAZINE UREA ADDUCTS

BACKGROUND OF THE INVENTION

The use of methylenephosphonic acid substituted alkylene polyamines for metal ion control at less than stoichiometric amounts was suggested in a patent to Bersworth (U.S. Pat. No. 2,609,390) in 1952. Later a water dispersible polymeric amine chelating agent which included alkylene phosphonate derivatives was indicated as having "threshold" effects in scale inhibition applications (U.S. Pat. No. 3,331,773), this term being used to describe the use of the agent in less than stoichiometric amounts. The diamine and polyamine methylenephosphonate derivatives are taught and claimed in U.S. Pat. Nos. 3,336,221 and 3,434,969, respectively. Some of the products disclosed in these two patents are available commercially and are recommended as scale inhibitors when applied in threshold amounts.

Some other patents which disclose heterocyclic nitrogen containing compounds which are useful as chelating agents and may be employed in threshold amounts are U.S. Pat. Nos. 3,674,804; 3,720,498; 3,743,603; 3,859,211; and 3,954,761. Some of the compounds included therein are heterocyclic compounds having the formulas:

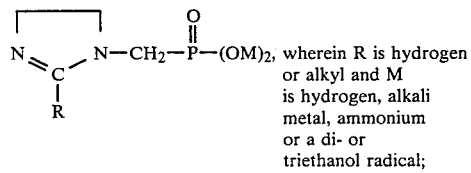

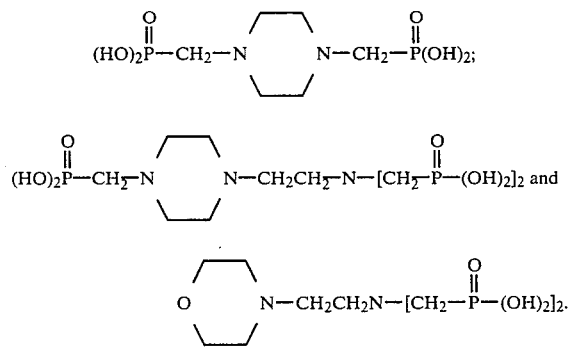

Methylenephosphonates of polyalkylene polyamines, disclosed in U.S. Pat. No. 4,051,110, are made by reacting di- or polyamines with a chain extending agent such as a dihalide or an epoxyhalide, e.g. ethylene dichloride or epichlorohydrin and thereafter, with phosphorous acid and formaldehyde. Thus, for example, triethylenetetramine is reacted with epichlorohydrin in an approximately one to one mole ratio; thereafter the product is reacted with phosphorous acid, and formaldehyde in the presence of hydrochloric acid. The resulting methylenephosphonated polyamine is useful in small amounts as a scale inhibitor, being employed at concentrations of 20–50 ppm.

Certain phosphonic acid derivatives of the aliphatic acids can be prepared by reacting phosphorous acid with acid anhydrides or acid chlorides, e.g. the anhydrides or chlorides of acetic, propionic and valeric acids. The compounds prepared have the formula

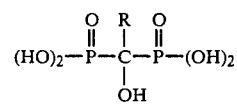

wherein R is a lower alkyl radical having 1 to 5 carbon atoms. The method of making and use of these products is described in U.S. Pat. No. 3,214,454. It discloses and claims the use of threshold amounts to prevent calcium precipitation in aqueous solutions.

SUMMARY OF THE INVENTION

It has now been found that certain methylene phosphonic acid derivatives of aminohydrocarbyl piperazine-urea adducts are good threshold agents to prevent metal ion precipitation in aqueous solutions.

DETAILED DESCRIPTION OF THE INVENTION

While the methylene phosphonate of aminoethylpiperazine itself has been shown not to have very good threshold activity, the analogous derivatives of the adducts of aminoethylpiperazine and urea are quite effective.

The compounds from which the methylenephosphonates are derived have the formula

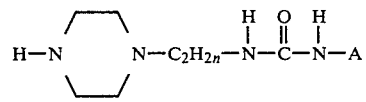

wherein A is

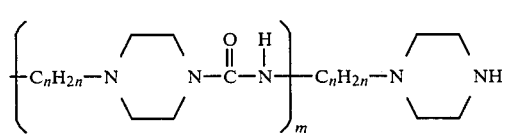

or hydrogen and where m is 0–2 and n is 2 or 3. These compounds are made by reacting urea with an aminohydrocarbylpiperazine. Thus, for example, aminoethylpiperazine (516.84 g, 4 moles) was added to a 1-liter reaction vessel equipped with a stirrer, reflux condenser, temperature control and indicating means was added 516.84 g (4 moles) of aminoethyl piperazine (AEP). After raising the temperature to about 120° C., 0.32 g (0.0039 mole) of 2-methylimidazole catalyst was added, immediately followed by the addition of 20 g (0.3 mole) of urea. After reacting for 2 hours at 120° C. while stirring, another 0.32 g (0.0039 mole) of 2-methylimidazole catalyst was added, followed by the addition of 40 g (0.7 moles) of urea. The progress of the reaction was monitored periodically by titration with 1N HCl employing bromthymol blue as an indicator. The titration results after 54.3 hours was the same as that after 17.4 hours at 120° C. The excess aminoethyl piperazine was removed by means of a rotoevaporator at a temperature of 120° C. and a pressure of 0.120 mm HgA. The product yield was >99% based on urea conversion and 93.3% based on net product weight. The amino hydrogen equivalent weight was determined to be 195.3. The product was a highly viscous straw colored mass.

The following example is representative of a preparation giving a crystalline product having predominantly a 1/1 mole ratio of AEP/urea.

To a 1-liter reaction flask equipped with a mechanical stirrer, thermometer, I²R temperature controller, and water cooled condenser was added 4.86 moles (4.86 equivalents of primary amine) or 628 grams of N-(2-aminoethyl)piperazine (AEP). Then 0.93 gram (0.12 wt% of total) of 2-methylimidazole was added as a catalyst. The reaction solution was then heated to 120° C. while stirring well and controlled at this temperature. Then 2.5 moles (5 equivalents) of urea was added manually in 4 increments over a 2.13 hours (7668 s) period. The reaction was allowed to digest at 120° C. for an additional 3.5 hours (12,600 s). Two small samples were taken during this time and titrated with 1N HCl using bromthymol blue as the indicator to determine the % conversion. The heat and stirrer was turned off and reaction solution allowed to cool to ambient temperature (~25° C.). About 80 volume % of the reaction flask crystallized. A sample of this crude product (crystals and liquid) was found to contain 48 area % 1-(2-piperazinoethyl)urea, 33 area % unreacted aminoethylpiperazine, and about 19 area % unknown impurities. The crude crystalline product (722 grams) was placed in a large vessel containing 1444 grams of acetone and stirred mechanically for 15 minutes (900 s). The crystalline product was then separated from the liquid phase by filtering through a medium sintered glass funnel using a vacuum flask. A second extraction was made using fresh acetone and filtered as before. The residual acetone was removed using a rotary evaporator at 30° to 40° C. and less than 1 mm Hg absolute pressure. A white crystalline solid was obtained having a melting point of 147° C. to 152° C. The amine nitrogen equivalent weight calculated by titrating with 1N HCl was 168.14 compared to 172.27 (theory). This product was greater than 90% pure as confirmed by liquid chromatography. Analysis by NMR and infrared were used to identify the product as 1-(2-piperazinoethyl) urea which can be represented by the following general formula

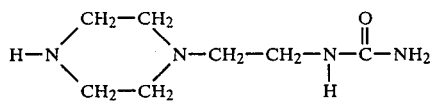

These compounds are disclosed and their method of preparation described in the copending application of Jimmy Myers et al (C-29,533) entitled "Adducts of Aminohydrocarbyl Piperazines and Urea", Ser. No. 514,761 filed July 18, 1983 and in the copending application of Jimmy Myers (C-30,415) entitled "Piperazinoethyl Ureas".

The products of the above reactions described in the above two copending applications are then phosphonomethylated to give the products of the present invention. The method of preparation is shown in Example 1 below. The adduct preferred is one which is completely phosphonomethylated. The most preferred is the completely phosphonomethylated adduct in which m is 0. These have the formula

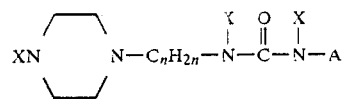

wherein n is 2 or 3 and A is

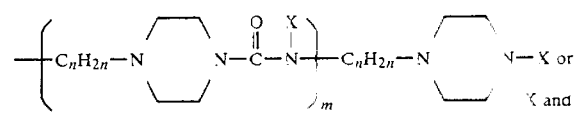

wherein X is

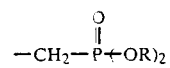

or H and wherein R is H, ammonium, an alkali or alkaline earth metal and m is 0–2, and wherein at least one X is

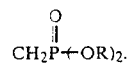

The following examples show the preparation of these compounds and their use as threshold agents.

EXAMPLE 1

One hundred fifty gm (0.53 mole) of an aminoethylpiperazine/urea (2/1 mole ratio) reaction product and 90 gm of deionized water were added to a 500 ml round-bottom reaction flask equipped with a water-cooled reflux condenser, mechanical stirrer, thermometer with a temperature controller, and an addition funnel. Approximately 200 gm of concentrated hydrochloric acid and 92 gm (1.1 moles) of phosphorous acid were added with stirring and the mixture heated to reflux and maintained for one hour. Paraformaldehyde (37 g—91%, 1.1 moles) was added over a one-hour period. The reaction mixture was heated at reflux for an additional two hours and then cooled. The product was evaluated as a scale inhibitor for calcium sulfate and compared to a commercially available scale inhibitor, aminotrimethylenephosphonic acid.

EXAMPLE 2

The aminoethylpiperazine/urea product employed in Example 1 was phosphonomethylated with approximately 4 mole equivalents of formaldehyde and phosphorous acid according to the general procedure of Example 1. The product was evaluated as a scale inhibitor.

EXAMPLE 3

An aminoethylpiperazine/urea reaction product (1/1 mole ratio) was phosphonomethylated using the general procedure of Example 1. The reaction product was evaluated for scale inhibition.

Results of scale inhibition for the products of Examples 1–3 are shown in Table I.

The test, the results of which are shown in Table I, is a standard calcium sulfate precipitation test described in "Laboratory Screening Tests to Determine the Ability of Scale Inhibitors to Prevent the Precipitation of Calcium Sulfate and Calcium Carbonate from Solution" published by the National Association of Corrosion Engineers, approved 1974. The test is identified as NACE Standard TM-03-74.

TABLE I

Calcium Sulfate Inhibition Data

| Additive | Concentration (ppm*) | % Ca++ in Solution at*** 24 Hrs | 48 Hrs | 72 Hrs |
|---|---|---|---|---|
| Example 1 | 1 | 99 | 97 | 97 |
| Example 2 | 1 | 100 | 99 | 98 |
| Example 3 | 1 | 98 | 97 | 96 |
| Commcl. Inhib.** | 1 | 84 | 81 | 79 |
| None (blank) | — | 69 | 66 | 64 |

*ppm based on active acid
**aminotrimethylenephosphonic acid
***original Ca++ concentration in solution was 5130 ppm CaSO4.

As previously indicated the completely phosphonomethylated adduct in which the AEP/urea mole ratio is 2/1 is especially effective (see Example 2, Table I).

We claim:

1. The compounds having the formula

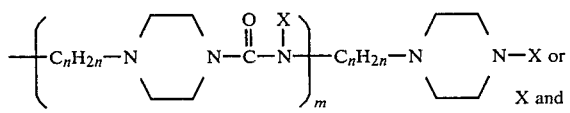

wherein A is

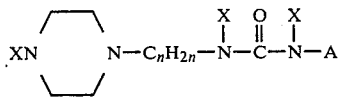

wherein X is

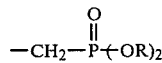

or H and wherein R is H, ammonium, an alkali or alkaline earth metal, m is 0-2, n is 2 or 3 and wherein at least one X is

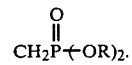

2. The compound of claim 1 wherein A is

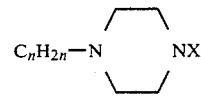

and each X is

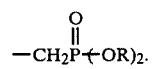

3. The compound of claim 1 wherein A is X.
4. The compound of claim 1 wherein R is hydrogen.
5. The compound of claim 2 wherein R is an alkaline earth metal.
6. The compound of claim 3 wherein R is an alkaline earth metal.
7. The compound of claim 2 wherein R is an alkali metal or ammonium.
8. The compound of claim 3 wherein R is an alkali metal or ammonium.
9. The compound of claim 5 wherein the alkaline earth metal is magnesium or calcium.
10. The compound of claim 6 wherein the alkaline earth metal is magnesium or calcium.
11. The compound of claim 2 wherein n is 2.
12. The compound of claim 3 wherein n is 2.
13. The compound of claim 4 wherein n is 2.
14. The compound of claim 5 wherein n is 2.
15. The compound of claim 6 wherein n is 2.
16. The compound of claim 7 wherein n is 2.
17. The compound of claim 8 wherein n is 2.
18. The compound of claim 9 wherein n is 2.
19. The compound of claim 10 wherein n is 2.

* * * * *

UNITED STATES PATENT AND TRADEMARK OFFICE
CERTIFICATE OF CORRECTION

PATENT NO.  : 4,518,777
DATED       : May 21, 1985
INVENTOR(S) : Druce K. Crump and David A. Wilson It is certified that error appears in the above—identified patent and that said Letters Patent is hereby corrected as shown below:

In the title on the cover page and at Col. 1, line 4, change "AMINOHYDROCARCARBYLPIPERAZINE" to --AMINOHYDROCARBYLPIPERAZINE--.

Col. 1, line 39, change "triethanol" to --triethanolamine--.

Col. 2, line 35, change the formula to read:

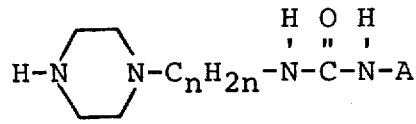

Signed and Sealed this

Twelfth Day of November 1985

[SEAL]

Attest:

Attesting Officer

DONALD J. QUIGG

Commissioner of Patents and Trademarks